(12) United States Patent
Kimura et al.

(10) Patent No.: US 10,308,906 B2
(45) Date of Patent: Jun. 4, 2019

(54) CELL CULTURE APPARATUS AND METHOD OF CULTURING CELLS

(71) Applicant: OLYMPUS CORPORATION, Hachioji-shi, Tokyo (JP)

(72) Inventors: Hiroyuki Kimura, Tokyo (JP); Tatsuya Minami, Kanagawa (JP); Yasunori Makara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/214,660

(22) Filed: Jul. 20, 2016

(65) Prior Publication Data

US 2017/0037352 A1 Feb. 9, 2017

(30) Foreign Application Priority Data

Aug. 4, 2015 (JP) ................... 2015-154201

(51) Int. Cl.
*C12M 1/26* (2006.01)
*C12M 1/00* (2006.01)
*C12M 3/00* (2006.01)

(52) U.S. Cl.
CPC ............ *C12M 23/44* (2013.01); *C12M 23/34* (2013.01); *C12M 29/00* (2013.01); *C12M 33/22* (2013.01)

(58) Field of Classification Search
CPC ...... C12M 23/44; C12M 23/34; C12M 29/00; C12M 33/22
See application file for complete search history.

(56) References Cited

U.S. PATENT DOCUMENTS 3,257,072 A 6/1966 Reynolds
4,137,285 A 1/1979 Nojiri et al.

FOREIGN PATENT DOCUMENTS

| CA | 2264206 A1 * | 2/1998 | ............ C12M 1/00 |
| JP | 52156983 A | 12/1977 | |
| JP | 2000125848 A | 5/2000 | |
| JP | 2011188777 A | 9/2011 | |

OTHER PUBLICATIONS

Partial European Search Report dated Dec. 21, 2016 issued in counterpart European Application No. 16181144.3.

* cited by examiner

*Primary Examiner* — Michael L Hobbs
(74) *Attorney, Agent, or Firm* — Holtz, Holtz & Volek PC

(57) ABSTRACT

A cell culture apparatus includes a culture tank having an inlet and an outlet, a culture-medium supplying unit that supplies a culture medium to the culture tank through the inlet, and a culture-medium discharging unit that discharges the culture medium through the outlet. The culture tank includes a division wall that can divide the internal space in a direction of gravity into an upper space and a lower space. The outlet opens into the upper space, and the division wall enables switching between a state where the internal space of the culture tank is divided into the upper space and the lower space and a state where the upper space and the lower space are in communication with each other.

14 Claims, 15 Drawing Sheets

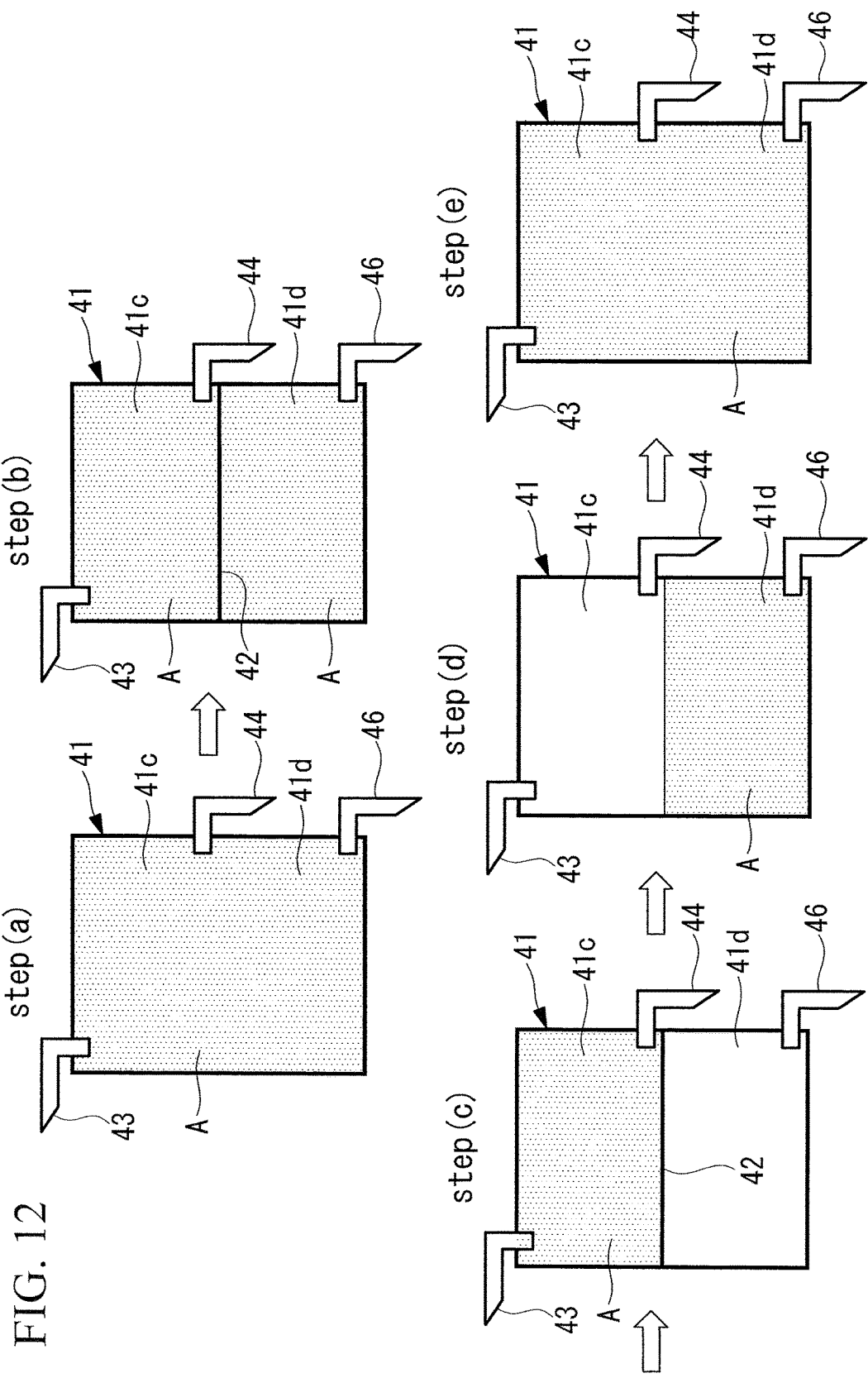

CELL CULTURE APPARATUS AND METHOD OF CULTURING CELLS

CROSS-REFERENCE TO RELATED APPLICATIONS

This application is based on Japanese Patent Application No. 2015-154201, filed on Aug. 4, 2015, the content of which is incorporated herein by reference.

TECHNICAL FIELD

The present invention relates to a cell culture apparatus and a method of culturing cells with which a culture medium in a culture system can be changed during cell Culture.

BACKGROUND ART

The mass culture of cells has recently been required with progression of stem cell research and regenerative medicine and development of biopharmaceuticals such as antibody drugs. Recent mass culture of cells uses culture tanks, such as bioreactors (see Patent Literature 1, for example), or cell culture bags (see Patent Literature 2, for example) made of gas-permeable materials, instead of flasks or petri dishes for cell culture.

Cells intake oxygen, nutrition, and other components needed for their growth and excrete carbon dioxide and waste products during cell culture. For this reason, culturing cells for a long period of time degrades culture media and requires culture media to be regularly changed.

To prepare clinically-used cells, for example, culture conforming to severe requirements is needed and thus culture in closed systems, which decreases contamination, is effective although the change of culture media in closed systems during cell culture is very difficult.

For the culture of floating cells, changing culture media requires separation of culture media and cells by centrifugation or other techniques.

CITATION LIST

Patent Literature

{PTL 1}
Japanese Unexamined Patent Application, Publication No. 2011-188777
{PTL 2}
Japanese Unexamined Patent Application, Publication No. 2000-125848

SUMMARY OF INVENTION

One aspect of the present invention is a cell culture apparatus including: a culture tank that can contain a culture medium and cells in its interior; a, culture-medium supplying unit that supplies the culture medium to the culture tank; and a culture medium discharging unit that discharges the culture medium from the culture tank. The culture tank includes a division wall that can divide an internal space of the culture tank in a direction of gravity into an upper space and a lower space, an inlet through which the culture-medium supplying unit supplies the culture medium to the interior, and an outlet through which the culture-medium discharging unit discharges the culture medium from the interior. The outlet opens into the upper space, and the division wall enables switching between a state where the internal space of the culture tank is divided into the upper space and the lower space and a state where the upper space and the lower space are in communication with each other.

Another aspect of the present invention is a method of culturing cells, comprising: a culturing step of culturing floating cells in a culture tank; a cell settling step of settling the floating cells in the culture tank; a space dividing step of dividing an internal space of the culture tank in a direction of gravity into an upper space and a lower space by using a division wall; a culture medium changing step of changing a culture medium in the upper space to a new culture medium.; and a space communication step of providing communication between the upper space and the lower space.

Another aspect of the present invention is a method of culturing cells, comprising: a culturing step of culturing floating cells in a culture tank; a cell settling step of settling the floating cells in the culture tank; a space dividing step of dividing an internal space of the culture tank in a direction of gravity into an upper space and a lower space by using a division wall; a collecting step of collecting a culture medium and the floating cells in the lower space; a space communication step of providing communication between the upper space and the lower space; and a culture medium supplying step of supplying a new culture medium to the upper space.

BRIEF DESCRIPTION OF DRAWINGS

FIG. 12 is a schematic diagram illustrating culture medium change using the cell culture apparatus according to the third embodiment of the present invention.

DESCRIPTION OF EMBODIMENTS (First Embodiment)

A cell culture apparatus according to the first embodiment of the present invention will now be described with reference to the attached drawings.

Figure 1A:
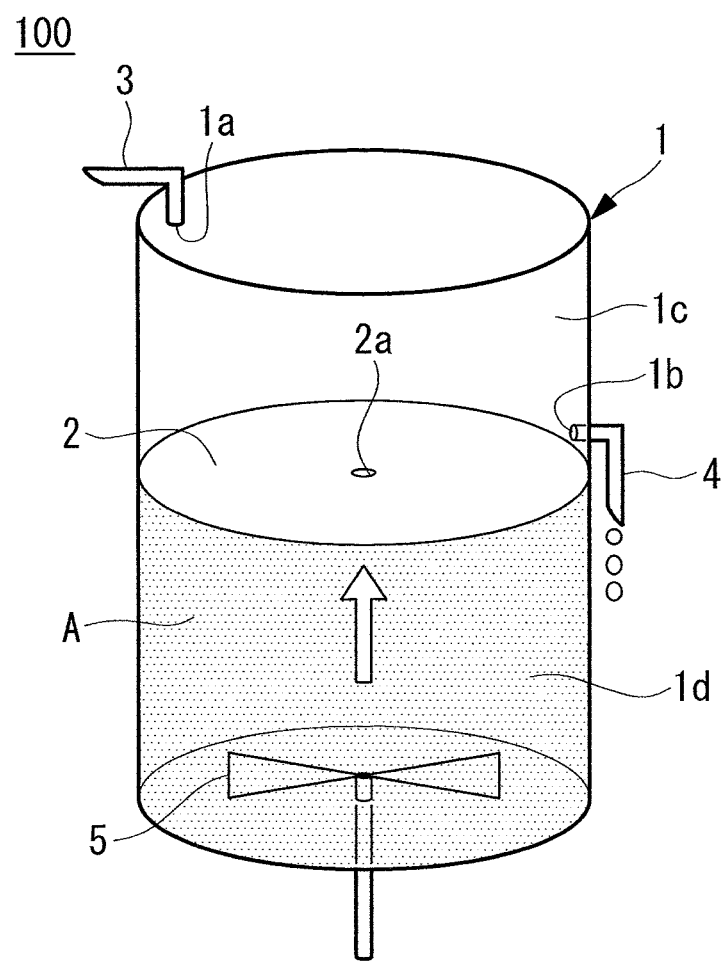
FIG. 1A is a schematic diagram illustrating the structure of a cell culture apparatus according to a first embodiment of the present invention.
Figure 1B:
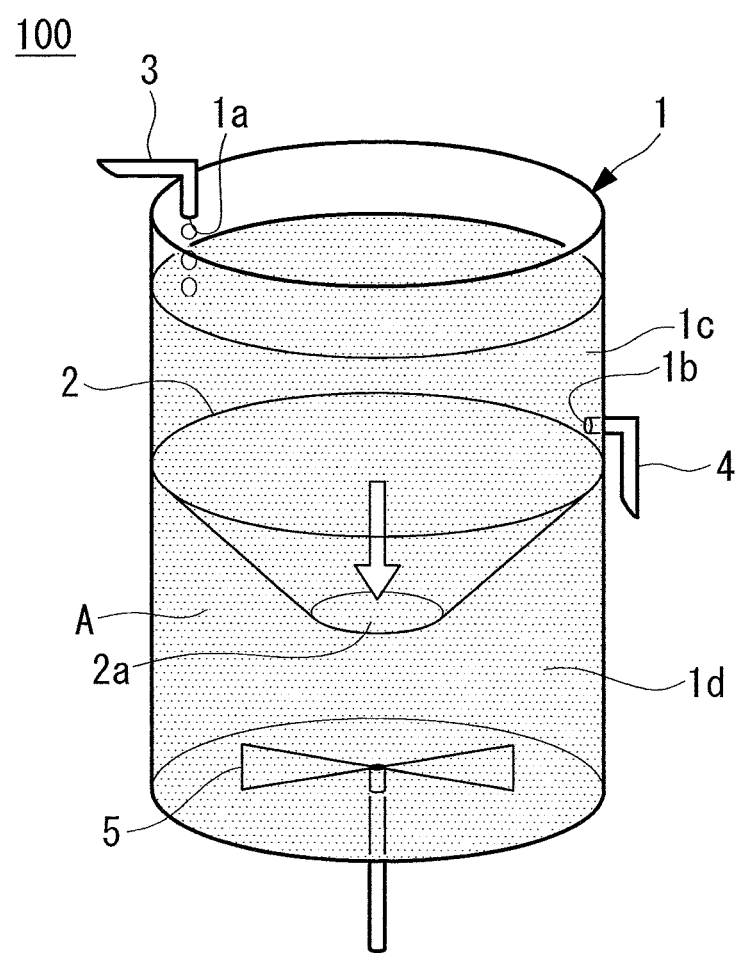
FIG. 1B illustrates the State where an opening in the cell culture apparatus in FIG. 1A is expanded and the upper space and the lower space are in communication with each other.

A cell culture apparatus 100 according to this embodiment is used to culture cells with a culture tank, such as a bioreator, and has a structure illustrated in FIGS. 1A and 1B.

The cell culture apparatus 100 includes a culture tank 1 that contains cells and a culture medium A held in its interior and that can culture cells while maintaining its internal environments in a state appropriate for cell culture, a culture-medium supplying unit 3 that supplies the culture medium A to the culture tank 1, and a culture-medium discharging unit 4 that discharges the culture medium A from the culture tank 1.

The culture tank 1 includes a bottom wall and a top wall facing each other, and a cylindrical side wall that connects the bottom wall and the top wall and extends in the direction of gravity. A sealed internal space is defined by the bottom wall, the top wall, and the side wall. The culture tank 1 is placed so that the bottom wall is located at a lower position in the direction of gravity and the top wall is located at an upper position in the direction of gravity. The culture tank 1 includes a division wall 2 dividing the internal space of the culture tank 1 in the direction of gravity into upper and lower spaces. The division wall 2 is substantially horizontally disposed inside the culture tank 1 so as to divide the interior of the culture tank 1 in the direction of gravity into an upper space 1c and a lower space 1d. The upper space 1c is a space upper than (on the top wall side of) he division wall 2, and the lower space 1d is a space lower than (on the bottom wall side of) the division wall 2.

At least a part of the division wall 2 is formed of an elastic member which has a small opening 2a. In a natural state with no external force applied to the elastic member, the opening 2a has such a small diameter that the cells and the culture medium A cannot pass it (see FIG. 1A). With external force applied to the elastic member, the opening 2a is expanded into a large size (see FIG. 1B) If the external force is removed, the opening 2a returns to a small size due to the elastic force of the elastic member.

If the opening 2a is large, the culture medium A and the cells can freely pass the opening 2a. If the opening 2a is small, the culture medium A and the cells are prevented from passing it.

An example of a method of applying external force to the elastic member of the division wall 2 will now be explained with reference to FIGS. 2A and 2B.

Figure 2A:
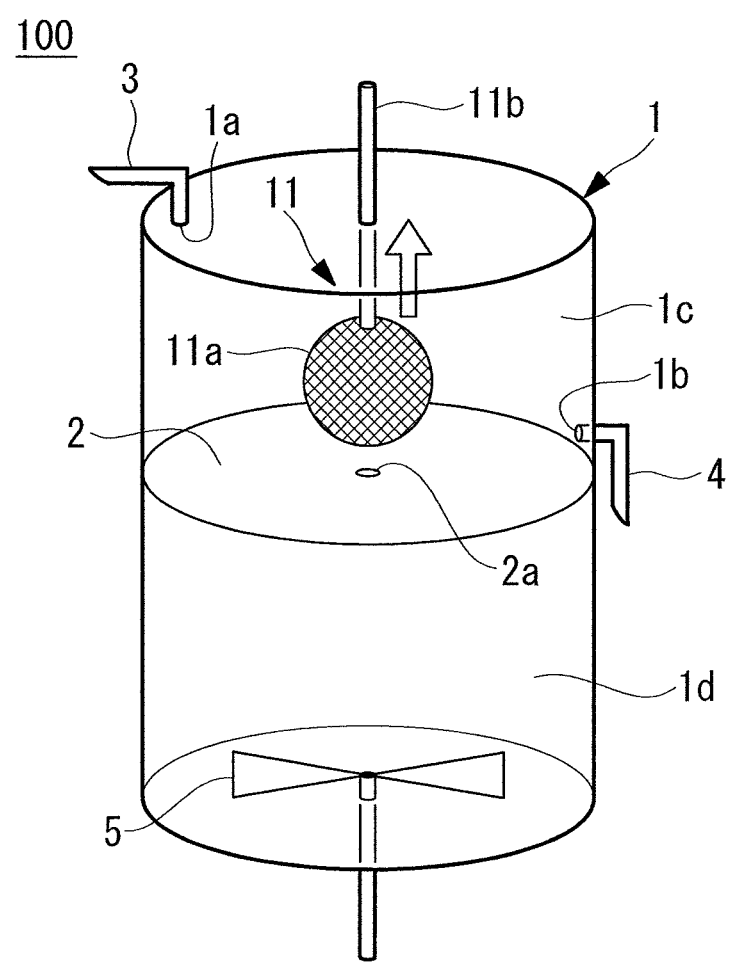
FIG. 2A is a schematic diagram illustrating the structure of a division wall in the cell culture apparatus according to the first embodiment of the present invention.
Figure 2B:
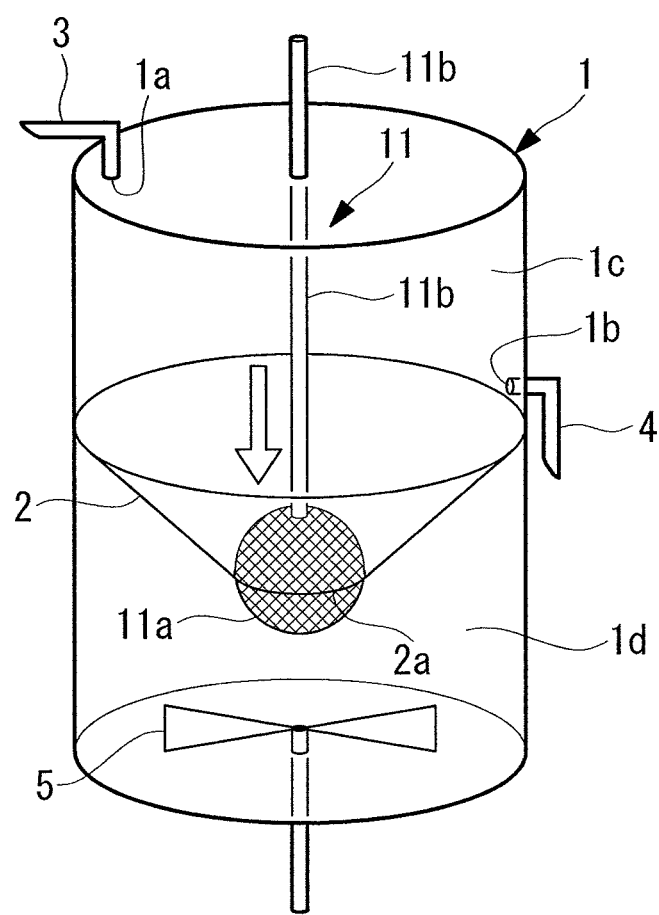
FIG. 2B illustrates the state where an opening in the division wall in FIG. 2A is expanded and the upper space and the lower space are in communication with each other.

FIGS. 2A and 2B illustrate the case where a division wall pushing unit 11 applies external pressure. The division wall pushing unit 11 includes a sphere unit 11a and a support rod 11b having a distal end coupled with the sphere unit 11a. When the sphere unit 11a is pushed against the opening 2a in the elastic member by the support rod 11b, the elastic member receives downward pressure and protrudes toward the lower space 1d and the sphere unit 11a extends the opening 2a.

The sphere unit 11a here forms an open space through which the culture medium A and the cells can freely pass, and the upper space 1c and the lower space 1d are in communication with each other through the sphere unit 11a. The sphere unit 11a is made of, for example, a mesh material that allows the culture medium A and the cells to freely pass therethrough, and has a strength to endure the pressure to extend the opening 2a. The sphere unit 11a does not necessarily have a sphere shape and may alternatively have a cone shape, for example.

Another example of the method of applying external force to the elastic member of the division wall 2 will now be described with reference to FIGS. 3A and 3B.

Figure 3A:
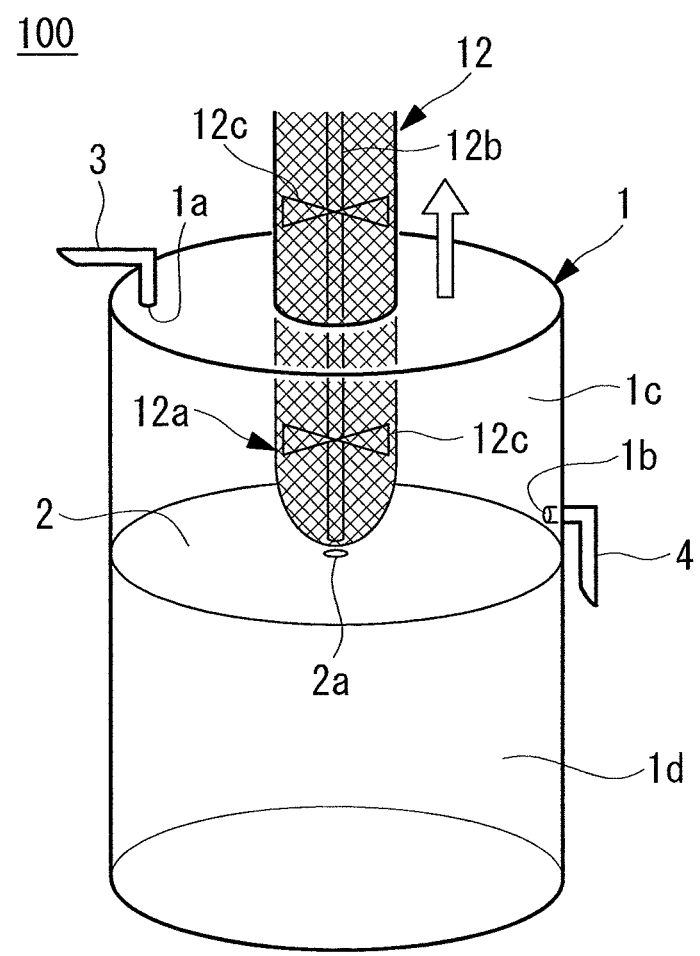
FIG. 3A is a schematic diagram illustrating the structure of a division wall of the cell culture apparatus according to the first embodiment of the present invention.
Figure 3B:
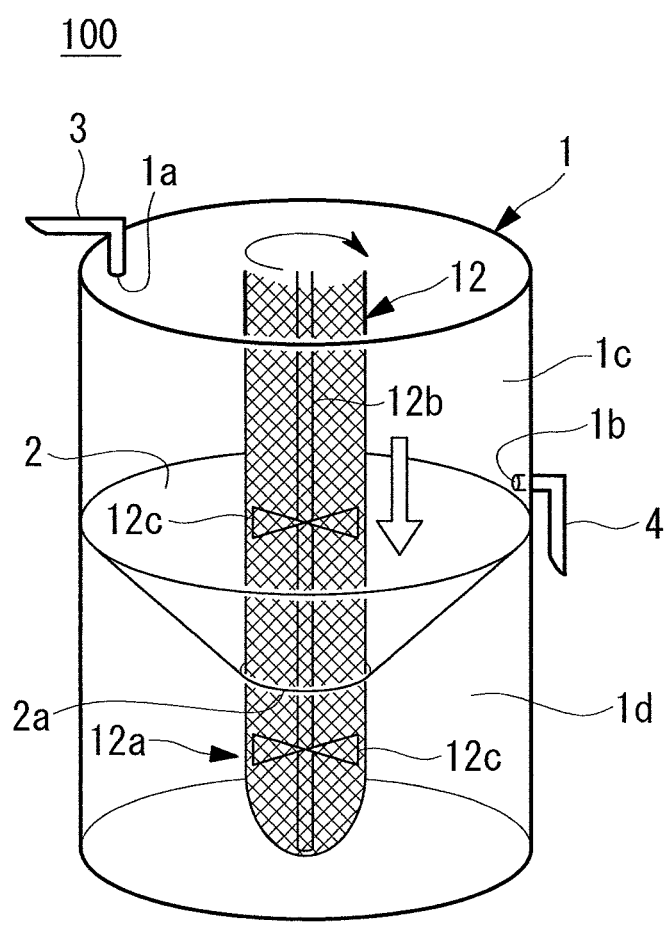
FIG. 3B illustrates the state where an opening in the division wall in FIG. 3A is expanded and the upper space and the lower space are in communication with each other.

FIGS. 3A and 3B illustrate the case Where the division wall pushing unit 12 applies external pressure. The division wall pushing unit 12 includes a cylinder unit 12a, a support rod 12b disposed inside the cylinder unit 12a, and a stirring unit 12c provided at the support red 12b.

When the distal end of the cylinder unit 12a is pushed against the opening 2a in the elastic member, the elastic member receives downward pressure and protrudes toward the lower space 1d, and, concurrently, the cylinder unit 12a extends the opening 2a. The cylinder unit 12a here forms an open space that allows the culture medium A and the cells to freely pass therethrough, and the upper space 1c and the lower space 1d can be in communication with each other through the cylinder unit 12a. The cylinder unit 12a is made of, for example, a mesh material that allows the culture medium A and the cells to freely pass therethrough, and has a strength to endure the pressure to extend the opening 2a. The stirring unit 12c in the cylinder unit 12a enables stirring of the culture medium A. For instance, the stirring unit 12c may be rotated by rotating the support rod 12b in order to stir the culture medium A.

The culture tank 1 includes an inlet 1a through which the culture medium A is supplied from the culture-medium supplying unit 3, and an outlet 1b through which the culture medium A is discharged to the culture-medium discharging unit 4. The inlet 1a and the outlet 1b open into the upper space 1c.

The outlet 1b preferably opens near the bottom of the upper space 1c so that almost all the culture medium A in the upper space 1c can be discharged.

The inlet 1a may be disposed in any position, but preferably opens into the position where it can drip the culture medium A from the upper portion of the upper space 1c. This can prevent the backflow of the culture medium A and reduce the risk of contamination of the upstream culture medium A. Although the inlet 1a opens into the upper space 1c in FIGS. 1A and 1B, the inlet 1a may alternatively open into the lower space 1d.

An example of a process of culturing cells using the cell culture apparatus 100 according to this embodiment will now be explained.

The user of the apparatus first pushes the elastic member of the division wall 2 by using the division wall pushing unit to provide communication between the upper space 1c and the lower space 1d through the division wall pushing unit. In this state, the culture medium A and the target cells (floating cells) are introduced into the culture tank 1 and cell culture is started while keeping the interior of the culture tank 1 at a temperature suitable for the cell culture (for example, 37° C.) (culturing step). At this time, the culture medium A and the cells are preferably stirred as appropriate with the use of the stirring unit 5.

When the culture medium A needs to be changed, the user first stops the stirring unit 5 to stop the flow of the culture medium A so that the cells can settle by gravity (cell settling step). The cells in the Upper space 1c sink toward the division wall 2, then slip toward the opening 2a because the elastic member protrudes toward the lower space 1d, pass through the opening 2a, and then settle on the bottom of the lower space 1d.

After the cells adequately settle, the user slowly pulls up the division wail pushing unit to release the external force applied to the elastic member and thus narrow the opening 2a, and divides the internal space of the culture tank 1 into the upper space 1c and the lower space 1d (space dividing step). At this time, almost all the cells settle in the lower space 1d and a few cells are left in the culture medium. A in the upper space 1c.

The user discharges the culture medium A in the upper space 1c from the culture tank 1 by using the culture-medium discharging unit 4, and then supplies a new culture medium A by using the culture-medium supplying unit 3 (culture medium changing step).

The user pushes the elastic member of the division wall 2 by using the division wall pushing unit to provide communication between the upper space 1c and the lower space 1d through the division wall pushing unit (space communication step). The stirring unit 5 is actuated to stir the culture medium A and the cells as appropriate and restart culture.

This process allows the culture medium A held in the upper space 1c to be changed to the new culture medium A, thereby slowing down the degradation of the culture medium A of the culture system. In addition, this allows floating cells and a culture medium to be separated through an easy procedure without a complicated procedure such as centrifugation. This simplifies the operation for culture medium change, reducing the workload of the operator and the risk of contamination of a cell culture system by bacteria, for example.

Figure 4:
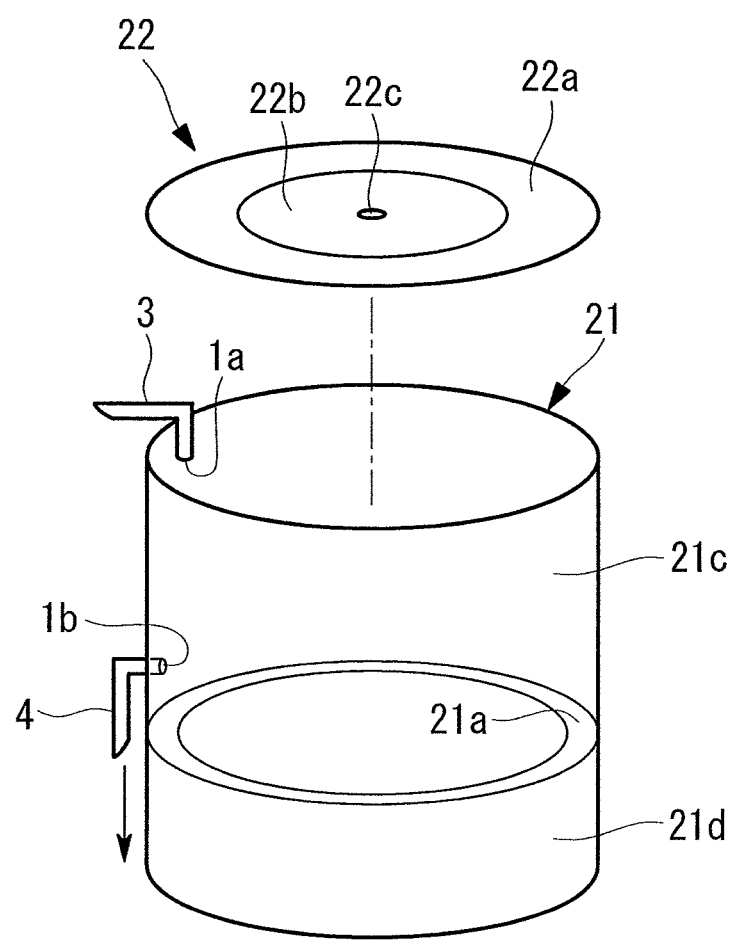
FIG. 4 is a schematic diagram illustrating the structure of a modification of the cell culture apparatus according to the first embodiment of the present invention.

A modification of this embodiment will now be described. A cell culture apparatus 200 according to this modification has a structure illustrated in FIG. 4.

In this modification, a division wall 22 can be separated from a culture tank 21. The division wall 22 includes a frame 22a and an elastic ember 22b fit in the frame 22a. The elastic member 22b includes an opening 22c. The frame 22a has a shape that can fit the interior of the culture tank 21.

A shelf portion 21a is fixed to the inner wall of the culture tank 21. When the division wall 22 is inserted in the culture tank 21, the frame 22a sits on the shelf portion 21a, so that the interior of the culture tank 21 can be divided into an upper space 21c and a lower space 21d.

Figure 5A:
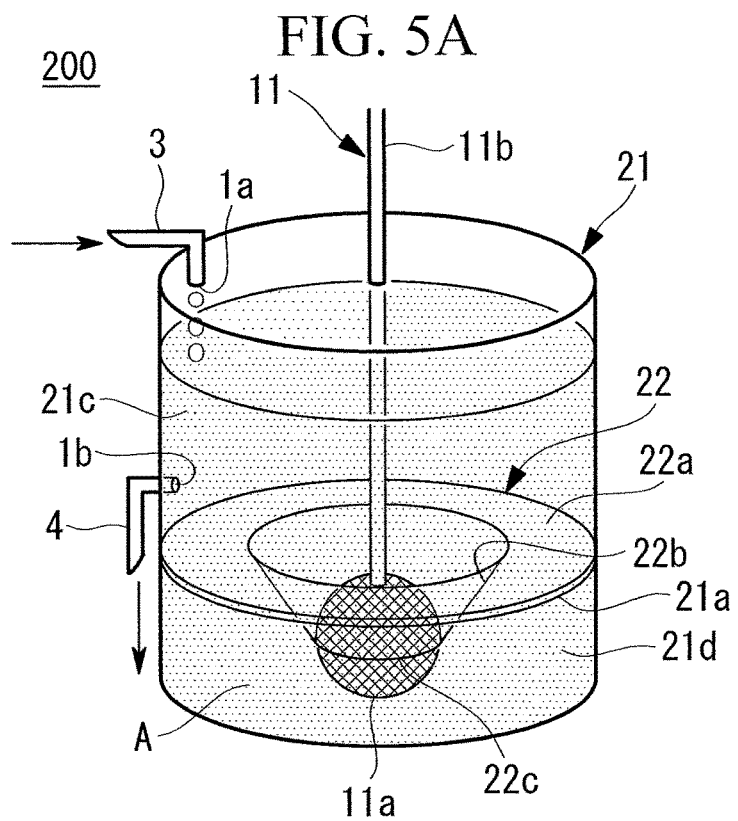
FIG. 5A is a schematic diagram illustrating the structure of a modification of the cell culture apparatus according to the first embodiment of the present invention.
Figure 5B:
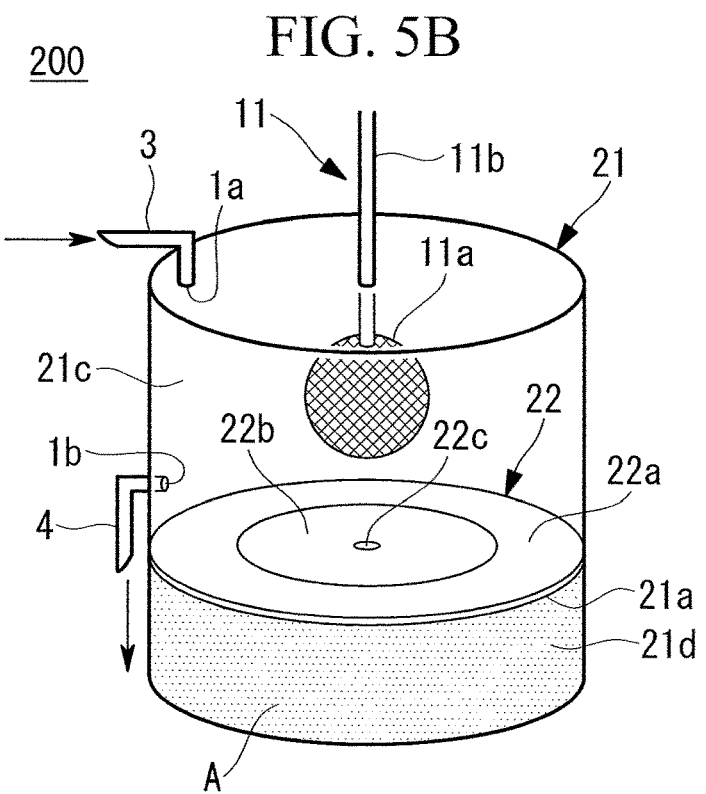
FIG. 5B illustrates the state where an opening in the cell culture apparatus in FIG. 5A is expanded and the upper space and the lower space are in communication with each other.

As illustrated in FIGS. 5A and 5B, the cell culture apparatus 200 enables cell culture in a manner similar to the cell culture apparatus 100 according to the first embodiment.

Although FIGS. 5A and 5B show the Case using the division wall pushing unit 11, the division wall pushing unit 12 may alternatively be used.

Figure 6:
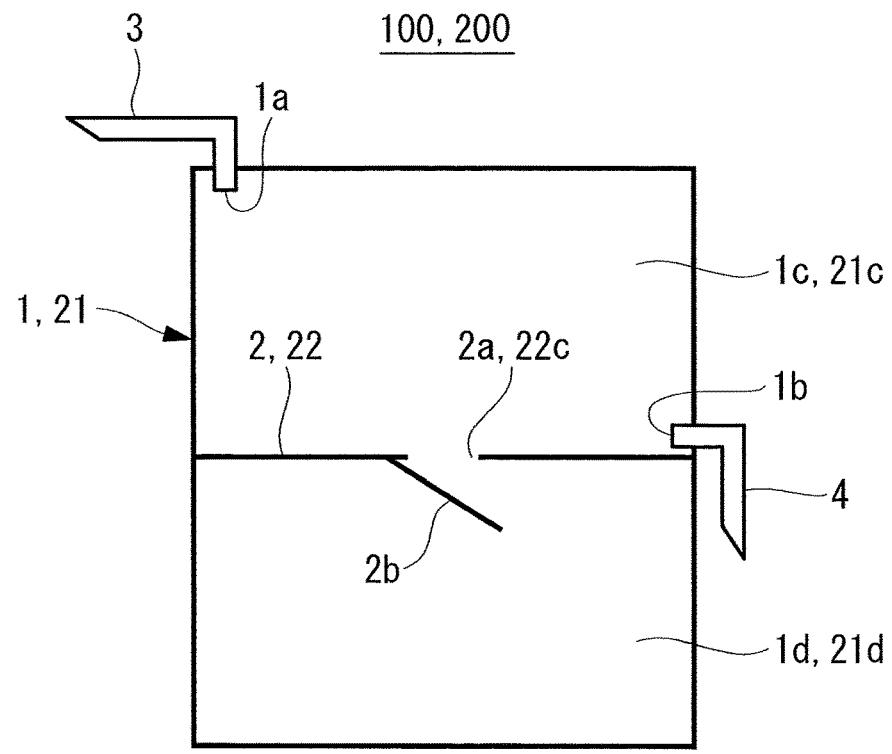
FIG. 6 is a schematic diagram illustrating the structure of a division wall of the cell culture apparatus according to the first embodiment of the present invention.

In these embodiment and modification, as illustrated in FIG. 6, the division wall 2 or 22 may include a valve 2b used to avoid the flow of the culture medium A from the lower space 1d or 21d to the upper space 1c or 21c. The valve 2b has a size that can cover the size of the opening 2a or 22c narrowed after the external force applied to the elastic member is removed. This can prevent the culture medium A from flowing from the lower space 1d or 21d toward the upper space 1c or 21c upon discharge of the culture medium A in the upper space 1c or 21c from the culture tank 1 or 21, thus reducing the risk of discharging cells.

Although these embodiment and modification show the case where the outlet 1b opens into the upper space, the outlet 1b may also open into the lower space. This facilitates the collection of the culture medium A and cells after the culture.

(Second Embodiment)

Figure 7:
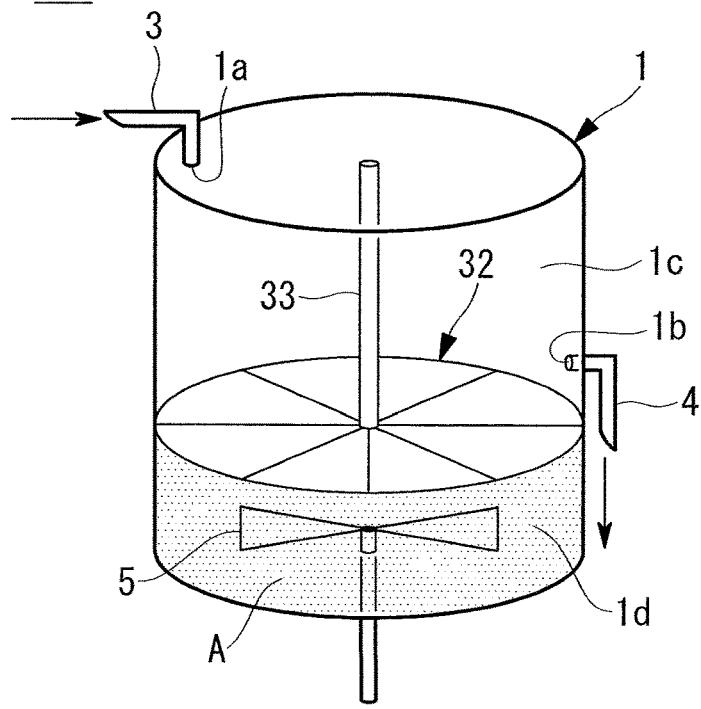
FIG. 7 is a schematic diagram illustrating the structure of a cell culture apparatus according to a second embodiment of the present invention.

A cell culture apparatus 300 according to the second embodiment of the present invention will now be described with reference to the attached drawings The cell culture apparatus 300 according to this embodiment has a structure illustrated in FIG. 7 and differs from the first embodiment in that it has a division wall 3 instead of the division wall 2. Aside from that, it is similar to the first embodiment.

The division wall 32 does not include an elastic member unlike the division wall 2 of the first embodiment. Moving the plate members of the division wall 32 can provide communication between the upper space 1c and the lower space 1d or separate these spaces 1c and 1d.

Figure 8A:
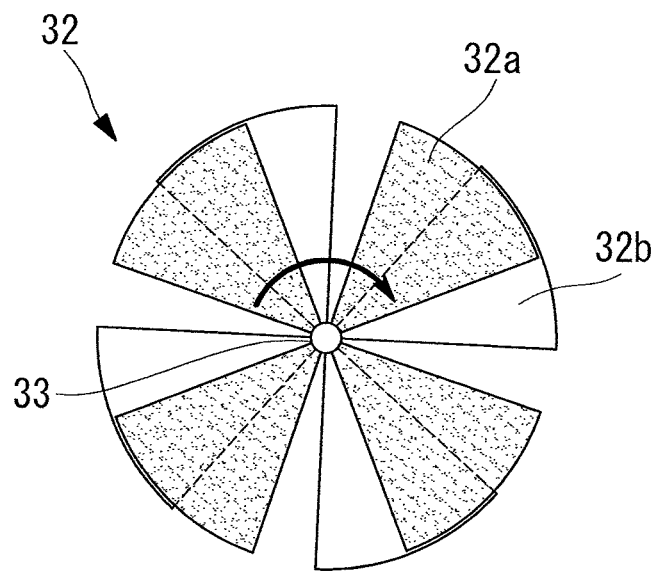
FIG. 8A is a schematic diagram illustrating the structure of a division wall of the cell culture apparatus according to the second embodiment of the present invention.
Figure 8B:
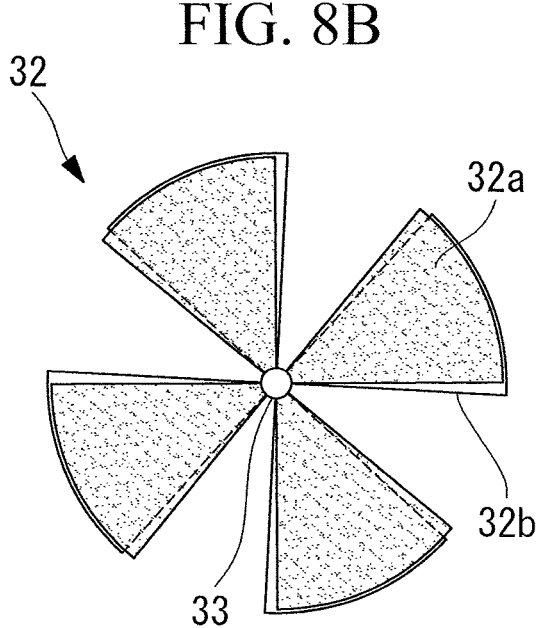
FIG. 8B illustrates the state where the division wall in FIG. 8A is opened to provide communication between the upper space and the lower space.
Figure 8C:
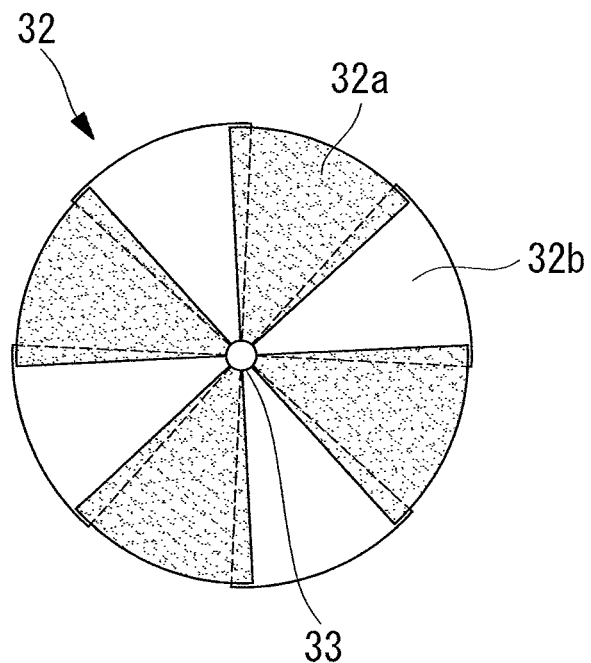
FIG. 8C illustrates the state where the division wall in FIG. 8A is closed to separate the upper space and the lower space.

An example of the division wall 32 is illustrated in FIGS. 8A to 8C. This division wall 32 includes two propeller-like plate members: a plate member 32a and a plate member 32b. The plate member 32a and the plate member 32b can rotate relatively to each other about a support rod 33 disposed substantially parallel with the direction of gravity. Rotating these two plate members 32a and 32b relatively to each other can provide communication between the upper space 1c and the lower space 1d (FIG. 8B) or separate the upper space 1c and the lower space 1d (FIG. 8C). In the state illustrated in FIG. 8B, the two plate members 32a and 32b overlap each other in the direction of gravity. In the state illustrated in FIG. 8C, the two plate members 32a and 32b are arranged without any space therebetween.

For instance, in a case where the plate member 32a is fixed to the inner wall of the culture tank 1 and the plate member 32b is fixed to the support rod 33, rotating them about the support rod 33 causes the plate member 32b to rotate relatively to the plate member 32a and brings about the state illustrated in FIG. 8B or 8C.

In order to dispose the plate members 32a and 32b and the support rod 33 in predetermined positions inside the culture tank 1, a shelf portion may be provided inside the culture tank 1 and the plate member 32a and 32b and the support rod 33 may be disposed on the shelf portion.

Figure 9A:
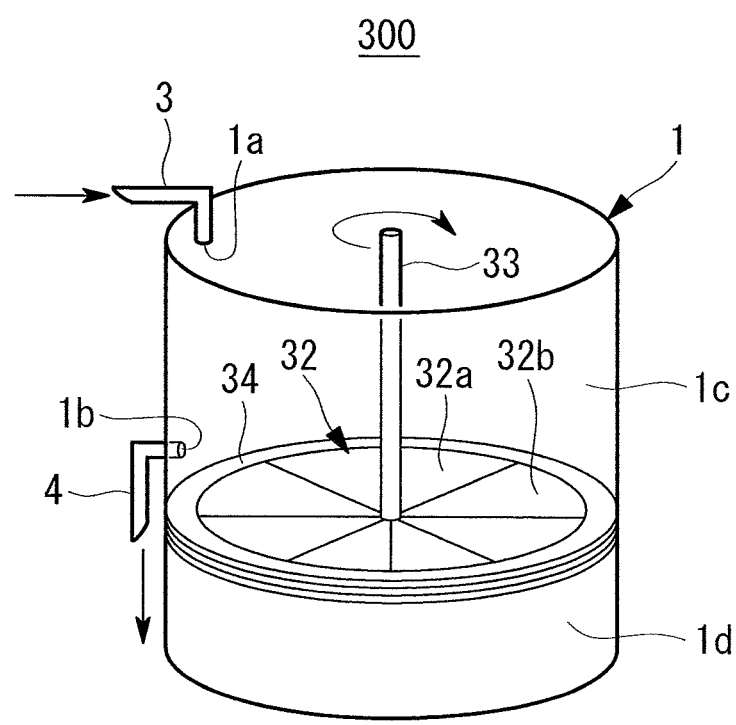
FIG. 9A is a schematic diagram illustrating the structure of a shelf portion of the cell culture apparatus according to the second embodiment of the present invention.
Figure 9B:
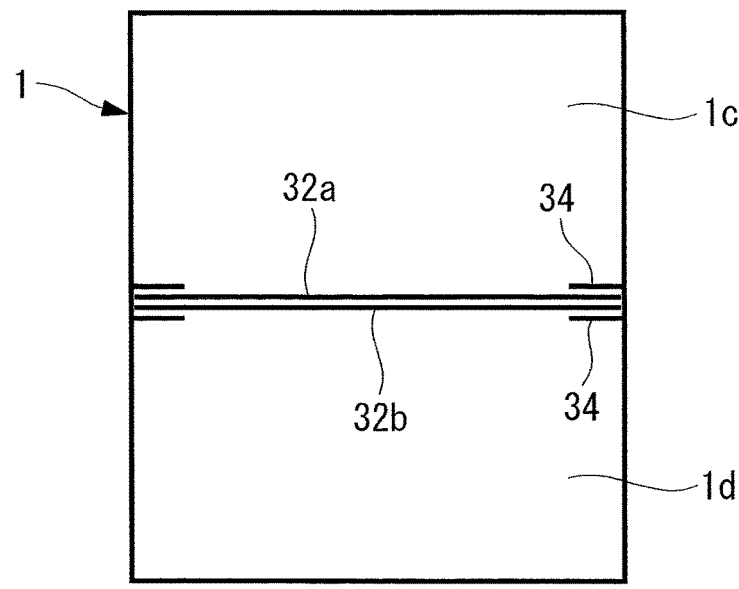
FIG. 9B illustrates a longitudinal section of a culture tank of the cell culture apparatus in FIG. 9A.

For instance, as illustrated in FIGS. 9A and 9B, the shelf portion may consist of two ring members 34 fixed to the inner wall of the culture tank 1 and vertically separated by a predetermined distance, and the plate member 32a and the plate member 32b may be disposed between the two ring members 34. At this time, the plate member 32a may be fixed to the ring member 34 and the plate member 32b fixed to the support rod 33 may be movably disposed between the two ring members 34. This allows the plate member 32b to rotate about the support rod 33 and brings about the state illustrated in FIG. 8B or 8C.

A process for culturing cells by using the cell culture apparatus 300 according to this embodiment will now be explained.

The user of the apparatus first rotates the support rod 33 to rotate the two plate members 32a and 32b relatively to each other and provide communication between the upper space 1c and the lower space 1d (FIG. 8B). In this state, the culture medium A and target cells (floating cells) are introduced into the culture tank 1 and cell culture is started while keeping the interior of the culture tank 1 at a temperature suitable for the cell culture (for example, 37° C.) (culturing step). At this time, the culture medium. A and the cells are preferably stirred as appropriate with the use of the stirring unit 5.

When the culture medium A needs to be changed, the user first stops the stirring unit 5 to stop the flow of the culture medium A so that the cells can settle by gravity (cell settling step). The cells in the upper space 1c pass through openings in the division wall 32 and then settle on the bottom of the lower space 1d.

After the cells adequately settle, the user rotates the support rod 33 to rotate the two plate members 32a and 32b relatively to each other and separate the upper space 1c and the lower space 1d (FIG. 8O) (space dividing step). At this time, almost all the cells settle in the lower space 1d and a few cells are left in the culture medium in the upper space 1c.

The user discharges the culture medium A in the upper space In from the culture tank 1 by using the culture-medium discharging unit 4, and then supplies a new culture medium A by using the culture-medium supplying unit 3 (culture medium changing step).

The user rotates the support rod 33 to rotate the two plate members 32a and 32b relatively to each other and provide communication between the upper space 1c and the lower space 1d (FIG. 8B) (space communication step). The stirring unit 5 is actuated to stir the culture medium and the cells as appropriate and restart culture.

This process allows the culture medium A held in the upper space 1c to be changed to the new culture medium A, thereby slowing down the degradation of the culture medium A of the culture system.

Figure 10A:
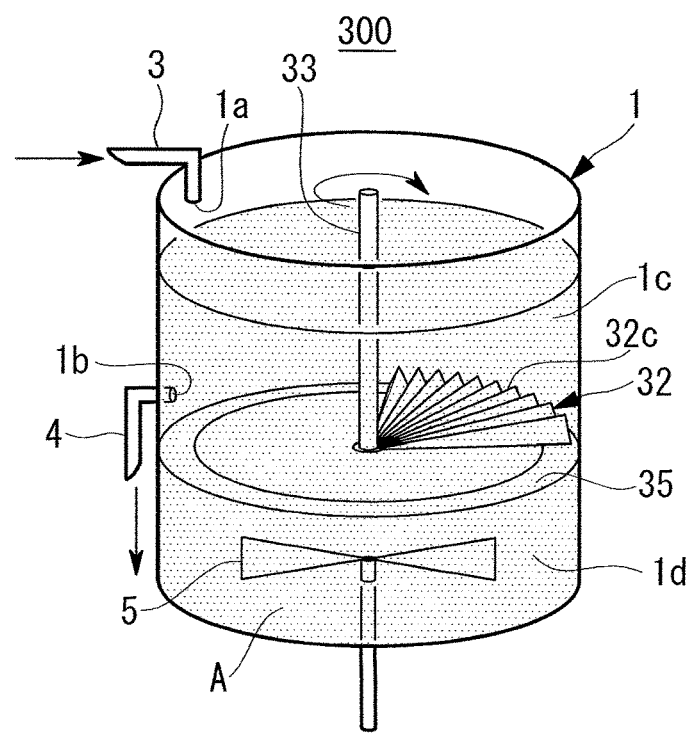
FIG. 10A is a schematic diagram illustrating the structure of a division wall of the cell culture apparatus according to the second embodiment of the present invention.
Figure 10B:
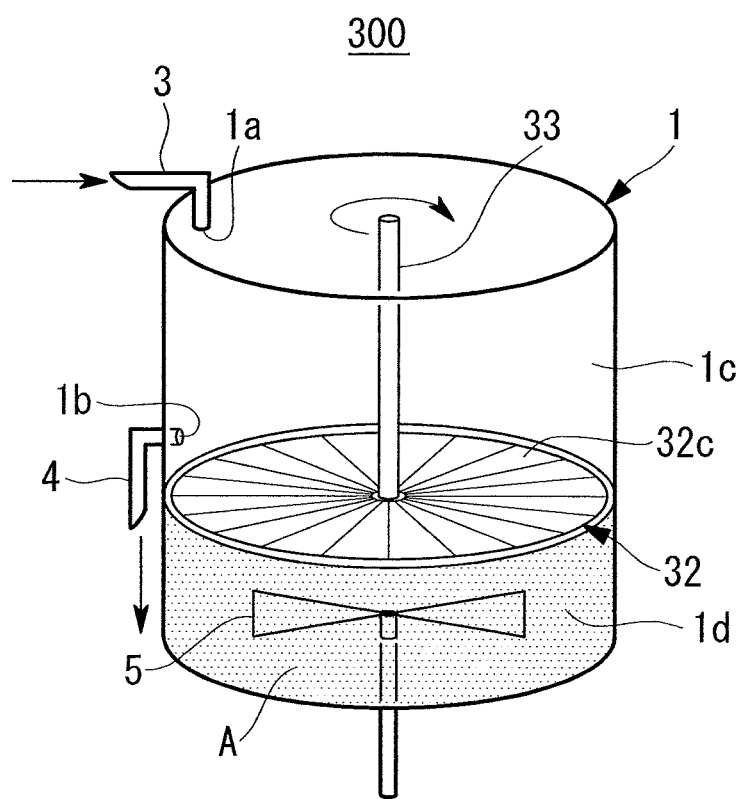
FIG. 10B illustrates the case where the division wall of the cell culture apparatus in FIG. 10A is opened.

Another example of the division wall 32 is illustrated in FIGS. 10A and 10B. This division wall 32 includes a plate member 32c that can be folded in an accordion manner. The plate member 32c is fixed to the support rod 33 and can spread or fold in the circumferential direction by rotation about the support rod 33. For example, with an end of the plate member 32c fixed to the inner wall of the culture tank 1, rotating the plate member 32c about the support rod 33 can spread or fold the plate member 32c like a folding fan and thus provide communication between the upper space 1c and the lower space 1d (FIG. 10A) or separate these spaces 1c and 1d (FIG. 10B).

A shelf portion 35 may be provided inside the culture tank 1 in order to dispose the plate member 32c and the support rod 33 in predetermined positions inside the culture tank 1.

(Third Embodiment)

A cell culture apparatus 400 according to the third embodiment of the present invention will now be described with reference to the attached drawings.

Figure 11:
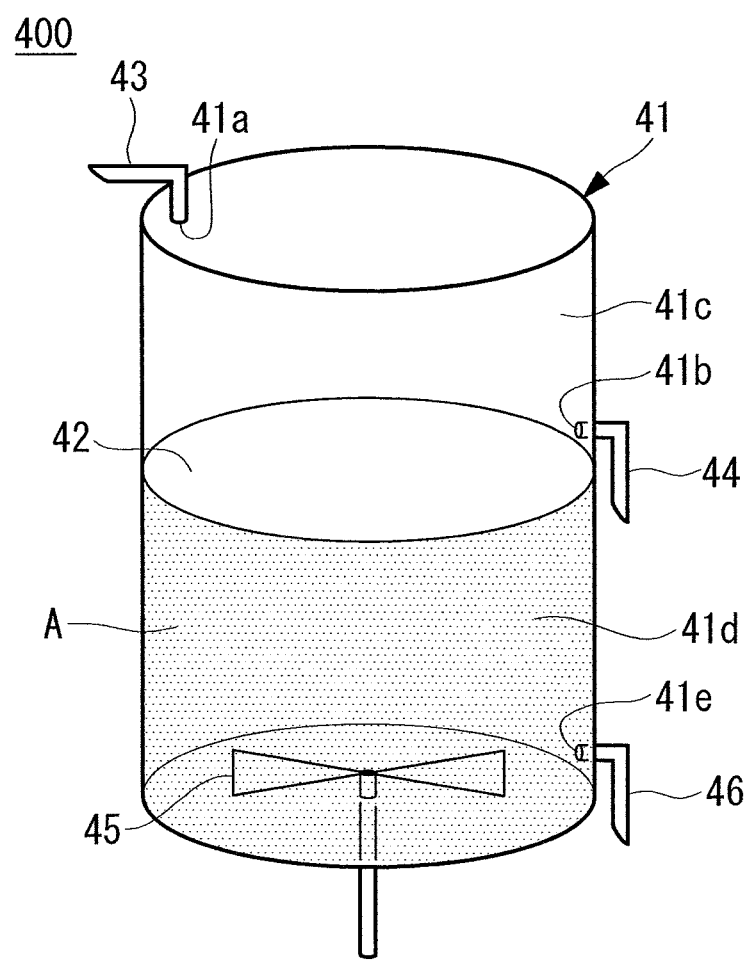
FIG. 11 is a schematic diagram illustrating the structure of a cell culture apparatus according to a third embodiment of the present invention.

The cell culture apparatus 400 according to this embodiment has a structure illustrated in FIG. 11 and differs from the above-described embodiments in that it also has an outlet 41e in the lower space 41d so that the culture medium A can be discharged to the culture-medium discharging unit 46 through the outlet 41e. Aside from that, this embodiment is similar to the above-described embodiments.

The cell culture apparatus 400 includes a culture tank 41 that contains cells and a culture medium A held in its interior and that can culture cells while maintaining its internal environments in a state appropriate for cell culture, a culture-medium supplying unit 43 that supplies the culture medium A to the culture tank 41, and culture-medium discharging unit 44 and 46 that discharge the culture medium A from the culture tank 41.

The culture tank 41 includes a division wall 42 dividing the internal space in the direction of gravity into upper and lower spaces. The division wall 42 is disposed inside the culture tank 41 so as to divide the interior of the culture tank 41 in the direction of gravity into an upper space 41c and a lower space 41d. The division wall 42 can be the same as any one of the division walls 2, 22, and 32 according to the first embodiment and the second embodiment.

The culture tank 41 includes an inlet 41a through which the culture medium A is supplied from the culture-medium supplying unit 43, an outlet 41b through which the culture medium A is discharged to the culture-medium discharging unit 44, and an outlet 41e through which the culture medium A is discharged to the culture-medium discharging unit 46. The inlet 41a and the outlet 41b open into the upper space 41c and the outlet 41e opens into the lower space 41d.

The outlet 41b preferably opens near the bottom of the upper space 41c so that almost all the culture medium A in the upper space 41c can be discharged. The outlet 41e preferably opens near the bottom of the lower space 41d so that almost all the culture medium A in the lower space 41d can be discharged.

The inlet 41a may be disposed in any position, but preferably opens in the position where it can drip the culture medium. A from the upper portion of the upper space 41c. This can prevent the backflow of the culture medium A. Although the inlet 41a opens into the upper space 41c in FIGS. 10A and 10B, the inlet 41a may alternatively open into the lower space 41d.

An example of a process of culturing cells using the cell culture apparatus 400 according to this embodiment will now be explained with reference to FIG. 12.

The user of the apparatus first opens an opening in the division wall 42 to provide communication between the upper space 41c and the lower space 41d. In this state, the culture medium A and the target cells (floating cells) are introduced into the culture tank 41 and cell Culture is started while keeping the interior of the culture tank 41 at a temperature suitable for the cell culture example, 37° C.) (culturing step (a)). At this time, the culture medium A and the cells are preferably stirred as appropriate with the use of the stirring unit 45.

When the culture medium A needs to be changed, the user first stops the stirring unit 45 to stop the flow of the culture medium A so that the cells can settle by gravity (cell settling step). The cells in the upper space 41c pass through the opening in the division wall 42 and then settle on the bottom of the lower space 41d.

After the cells adequately settle, the user closes the opening in the division wall 42 to divide the culture tank 41 into the upper space 41c and the lower space 41d (space dividing step (b)). At this time, almost all the cells settle in the lower space 41d and a few cells are left in the culture medium A in the upper space 41c.

The user collects the culture medium A and cells present in the lower space 41d from the culture tank 41 by using the culture-medium discharging unit 46 (collecting step (c)).

The user opens the opening in the division wail 42 to provide communication between the Upper space 41c and the lower apace 41d and move the culture medium A present in the upper space 41c to the lower space 41d (space communication step (d)).

The user supplies a new culture medium A to the culture tank 41 by using the culture-medium supplying unit 43 (culture medium supplying step (e)) and actuates the stirring unit 45 to stir the culture medium A and the cells as appropriate and restart the culture.

This process enables collection of the cells settling in the lower space 41d so that the cell culture can continue with the cells left in the upper space 41c (which step corresponds to subculture of the cells). At this time, the amount of the culture medium A discharged from the lower space 41d can be changed to the corresponding amount of a new culture medium A, slowing down degradation of the culture medium A of the culture system.

The culture tank in the present invention may be either a large container like a bioreactor or a small container like a flask. Alternatively, a cell culture bag may be used as a single-use bioreactor.

The present invention provides a method of culturing floating cells with the use of a culture tank that can contain a culture medium and cells in its interior and includes a division wall that enables switching between the state where the internal space is divided in the direction of gravity into an upper space and a lower space and the state where the upper space and the lower space are in communication with each other, the method involving repetition of the following steps SA1 to SA5.

(SA1) A step of culturing floating cells in a culture tank.
(SA2) A step of settling the floating cells.
(SA3) A step of dividing the internal space of the culture tank in the direction of gravity into the upper space and the lower space with the use of the division wall.
(SA4) A step of changing the culture medium in the upper space to a new culture medium.
(SA5) A step of providing communication between the upper space and the lower space.

The present invention provides a method of culturing floating cells with the use of a culture tank that can contain a culture medium and cells in its interior and includes a division wall that enables switching between the state where the internal space is divided in a direction of gravity into an upper space and a lower space and the state where the upper space and the lower space are in communication with each other, the method involving repetition of the following steps SB1 to SB6.

(SB1) A step of culturing floating cells in a culture tank.
(SB2) A step of settling the floating cells.
(SB3) A step of dividing the internal space of the culture tank in a direction of gravity into the upper space and the lower space with the use of the division wall.
(SB4) A step of collecting the culture medium and cells in the lower space.
(SB5) A step of providing communication between the upper space and the lower space.
(SB6) A step of supplying a new culture medium to the upper space.

From the above-described embodiments and modifications thereof, the following aspects of the invention are derived.

One aspect of the present invention is a cell culture apparatus including: a culture tank that can contain a culture medium and cells in its interior; a culture-medium supplying unit that supplies the culture medium to the culture tank; and a culture-medium discharging unit that discharges the culture medium from the culture tank. The culture tank includes a division wall that can divide an internal space of the culture tank in a direction of gravity into an upper space and a lower space, an inlet through which the culture-medium supplying unit supplies the culture medium to the interior, and an outlet through which the culture-medium discharging unit discharges the culture medium from the interior. The outlet opens into the upper space, and the division wall enables switching between a state where the internal space of the culture tank is divided into the upper space and the lower space and a state where the upper space and the lower space are in communication with each other.

This aspect enables easy change of the culture medium for the mass culture of floating cells. Specifically, it enables culture medium change without separation of floating cells by a complicated procedure, such as centrifugation.

In the above aspect, the division wall may include an elastic member having an opening, the opening may be expanded and the upper space and the lower space may be in communication with each other while external force is applied to the elastic member, and the opening may be narrowed and the upper space and the lower space may be separated while no external force is applied to the elastic member. Thus, the upper space and the lower space can be easily separated and he floating cells and the culture medium can be separated with a simple structure.

In the above aspect, a valve that closes the opening in the elastic member from the lower Space side may be included. This stops the flow of the culture medium from the lower space toward the upper space when the culture medium is discharged from the upper space, reducing the risk of the outflow of the cells.

In the above aspect, a division wall pushing unit may be included which extends the opening in the elastic member and that is made of a mesh material that allows the culture medium and the cells to freely pass therethrough. Thus, the upper space and the lower space can be easily separated and the floating cells and the culture medium can be separated with a simple structure.

In the above aspect, the division wall may include a plurality of plate members and changing relative positions of the plurality of plate members may enable switching between a state where the internal space of the culture tank is divided into the upper space and the lower space and a state where the upper space and the lower space are communication with each other. Thus, the upper space and the lower space can be easily separated and the floating cells and the culture medium can be separated with a simple structure.

In the above aspect, the division wall may include a plate member that can be folded in an accordion manner, the internal space of the culture tank is divided into the upper space and the lower space by spreading the plate member, and the upper space and the lower space are communicated with each other by folding the plate member. Thus, the upper space and he lower space can be easily separated and the floating cells and the culture medium can be separated with a simple structure.

In the above aspect, the division wall may include a plate member fixed to a support rod and rotating the plate member about the support rod may enable switching between a state where the internal space of the culture tank is divided into the upper space and the lower space and a state where the upper space and the lower space are in communication with each other. Thus, the upper space and the lower space can be easily separated and the floating cells and the culture medium can be separated with a simple structure.

Another aspect of the present invention is a method of culturing cells, comprising: a culturing step of culturing floating cells in a culture tank; a cell settling step of settling the floating cells in the culture tank; a space dividing step of dividing an internal space of the culture tank in a direction of gravity into an upper space and a lower space by using a division wall; a Culture medium changing step of changing a culture medium in the upper space to a new culture medium; and a space communication step of providing communication between the upper space and the lower space.

Another aspect of the present invention is a method of culturing cells, comprising: a culturing step of culturing floating cells in a culture tank; a cell settling step of settling the floating cells in the culture tank; a space dividing step of dividing an internal space of the culture tank in a direction of gravity into an upper space and a lower space by using a division wall; a collecting step of collecting a culture medium and the floating cells in the lower space; a space communication step of providing communication between the upper space and the lower space; and a culture medium supplying step of supplying a new culture medium to the upper space.

REFERENCE SIGNS LIST 1, 21, 41 culture tank
1a, 41a inlet
1b, 14b outlet
2, 22, 32, 42 division wall
3, 43 culture-medium supplying unit
4, 44, 46 culture-medium discharging unit
5, 45 stirring unit
11, 12 division wall pushing unit
32a, 32b, 32c plate member
33 support rod
34 ring member
35 shelf portion

The invention claimed is:
1. A cell culture apparatus comprising:
a culture tank that can contain a culture medium and cells in its interior;
a culture-medium supply path to supply the culture medium to the culture tank; and
a culture-medium discharge path to discharge the culture medium from the culture tank,
wherein the culture tank comprises:
a division wall that selectively divides an internal space of the culture tank in a direction of gravity into an upper space and a lower space,
an inlet through which the culture-medium supply path supplies the culture medium to the interior, and
an outlet through which the culture-medium discharge path discharges the culture medium from the interior,
wherein the outlet opens into the upper space, and
wherein the division wall includes a plurality of plate members, and changing relative positions of the plurality of plate members enables switching between a state where the internal space of the culture tank is divided into the upper space and the lower space and a state where the upper space and the lower space are in communication with each other.

2. The cell culture apparatus according to claim 1, wherein the plurality of plate members include a first plate member that is fixed to a support rod, and rotating the first plate member about the support rod enables switching between the state where the internal space of the culture tank is divided into the upper space and the lower space and the state where the upper space and the lower space are in communication with each other.

3. The cell culture apparatus according to claim 2, wherein the plurality of plate members comprise:
the first plate member that is fixed to and rotatable about the support rod; and
a second plate member that is fixed to an inner wall of the culture tank.

4. The cell culture apparatus according to claim 3, wherein the culture tank further comprises, in the lower space, a stirrer to stir the cells and the culture medium.

5. The cell culture apparatus according to claim 4, wherein the culture tank further comprises, in the lower space, a further outlet.

6. The cell culture apparatus according to claim 1, wherein the culture tank further comprises a shelf provided inside the culture tank, and
wherein the plurality of plate members of the division wall are disposed on the shelf.

7. The cell culture apparatus according to claim 1, wherein the culture tank further comprises two ring members fixed to an inner wall of the culture tank, and
wherein the plurality of plate members of the division wall are disposed between the two ring members.

8. A culture tank that can contain a culture medium and cells in its interior, the culture tank comprising:
a division wall that selectively divides an internal space of the culture tank in a direction of gravity into an upper space and a lower space;
an inlet through which the culture medium can be supplied to the interior; and
an outlet through which the culture medium can be discharged from the interior,
wherein the outlet opens into the upper space, and
wherein the division wall includes a plurality of plate members, and changing relative positions of the plurality of plate members enables switching between a state where the internal space of the culture tank is divided into the upper space and the lower space and a state where the upper space and the lower space are in communication with each other.

9. The culture tank according to claim 8, wherein the plurality of plate members include a first plate member that is fixed to a support rod, and rotating the first plate member about the support rod enables switching between the state where the internal space of the culture tank is divided into the upper space and the lower space and the state where the upper space and the lower space are in communication with each other.

10. The culture tank according to claim 9, wherein the plurality of plate members comprise:
the first plate member that is fixed to and rotatable about the support rod; and
a second plate member that is fixed to an inner wall of the culture tank.

11. The culture tank according to claim 10, wherein further comprising, in the lower space, a stirrer to stir the cells and the culture medium.

12. The culture tank according to claim 11, further comprising, in the lower space, a further outlet.

13. The culture tank according to claim 8, further comprising a shelf provided inside the culture tank,
   wherein the plurality of plate members of the division wall are disposed on the shelf.

14. The culture tank according to claim 8, further comprising two ring members fixed to an inner wall of the culture tank,
   wherein the plurality of plate members of the division wall are disposed between the two ring members.

* * * * *